United States Patent
Wei et al.

(10) Patent No.: US 7,851,209 B2
(45) Date of Patent: Dec. 14, 2010

(54) REDUCTION OF THE HOOK EFFECT IN ASSAY DEVICES

(75) Inventors: Ning Wei, Roswell, GA (US); Yanbin Huang, Roswell, GA (US); Kaiyuan Yang, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 356 days.

(21) Appl. No.: 10/406,631

(22) Filed: Apr. 3, 2003

(65) Prior Publication Data

US 2004/0197820 A1    Oct. 7, 2004

(51) Int. Cl.
*C12M 1/34* (2006.01)

(52) U.S. Cl. .............. 435/288.7; 435/286.5; 435/287.7; 436/528; 436/533; 436/535; 427/2.11; 427/2.13

(58) Field of Classification Search ............ 435/4–7.92, 435/188, 283.1–287.1; 436/169, 501; 422/55, 422/56; 430/1, 2
See application file for complete search history.

(56) References Cited

U.S. PATENT DOCUMENTS

| | | |
|---|---|---|
| 164,659 A | 6/1875 | Reckhow et al. |
| 4,094,647 A | 6/1978 | Deutsch et al. |
| 4,110,529 A | 8/1978 | Stoy |
| 4,115,535 A | 9/1978 | Giaever |
| 4,168,146 A | 9/1979 | Grubb et al. |
| RE30,267 E | 5/1980 | Bruschi |
| 4,210,723 A | 7/1980 | Dorman et al. |
| 4,235,601 A | 11/1980 | Deutsch et al. |
| 4,275,149 A | 6/1981 | Litman et al. |
| 4,312,228 A | 1/1982 | Wohltjen |
| 4,361,537 A | 11/1982 | Deutsch et al. |
| 4,363,874 A | 12/1982 | Greenquist |
| 4,366,241 A | 12/1982 | Tom et al. |
| 4,374,925 A | 2/1983 | Litman et al. |
| 4,385,126 A | 5/1983 | Chen et al. |
| 4,426,451 A | 1/1984 | Columbus |
| 4,427,836 A | 1/1984 | Kowalski et al. |

(Continued)

FOREIGN PATENT DOCUMENTS

EP    0073593 A1    3/1983

(Continued)

OTHER PUBLICATIONS

Saitoh et al, Opening up of liposomal membranes by talin, 1998, Proc Natl Acad Sci USA, 95, 1026-1031.*

(Continued)

*Primary Examiner*—N C Yang
(74) *Attorney, Agent, or Firm*—Dority & Manning, P.A.

(57) ABSTRACT

A membrane-based assay device for detecting the presence or quantity of an analyte residing in a test sample is provided. The device utilizes conjugated probes that contain a specific binding member for the analyte of interest. The specific binding member preferentially complexes with the analyte within a test sample when contacted therewith. Excess analyte that remains uncomplexed with the specific binding member undergoes non-specific binding, such as to a hydrophobic domain. As a result, the ability of the uncomplexed analyte to compete with the complexed analyte at the detection zone of the device is restricted. Thus, the incidence of "false negatives" is limited in a simple, efficient, and relatively inexpensive manner.

15 Claims, 5 Drawing Sheets

U.S. PATENT DOCUMENTS

| | | | |
|---|---|---|---|
| 4,435,504 A | 3/1984 | Zuk et al. |
| 4,441,373 A | 4/1984 | White |
| 4,442,204 A | 4/1984 | Greenquist et al. |
| 4,444,592 A | 4/1984 | Ludwig |
| 4,477,635 A | 10/1984 | Mitra |
| 4,480,042 A | 10/1984 | Craig et al. |
| 4,533,499 A | 8/1985 | Clark et al. |
| 4,533,629 A | 8/1985 | Litman et al. |
| 4,534,356 A | 8/1985 | Papadakis |
| 4,537,861 A | 8/1985 | Elings et al. |
| 4,540,659 A | 9/1985 | Litman et al. |
| 4,552,458 A | 11/1985 | Lowne |
| 4,561,286 A | 12/1985 | Sekler et al. |
| 4,562,157 A | 12/1985 | Lowe et al. |
| 4,595,661 A | 6/1986 | Cragle et al. |
| 4,596,697 A | 6/1986 | Ballato |
| 4,614,723 A | 9/1986 | Schmidt et al. |
| 4,632,559 A | 12/1986 | Brunsting |
| 4,661,235 A | 4/1987 | Krull et al. |
| 4,698,262 A | 10/1987 | Schwartz et al. |
| 4,703,017 A * | 10/1987 | Campbell et al. ........... 436/501 |
| 4,714,682 A | 12/1987 | Schwartz |
| 4,722,889 A | 2/1988 | Lee et al. |
| 4,727,019 A | 2/1988 | Valkirs et al. |
| 4,731,337 A | 3/1988 | Luotola et al. |
| 4,743,542 A | 5/1988 | Graham, Jr. et al. |
| 4,776,944 A | 10/1988 | Janata et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,844,613 A | 7/1989 | Batchelder et al. |
| 4,849,338 A | 7/1989 | Litman et al. |
| 4,855,240 A | 8/1989 | Rosenstein et al. |
| 4,857,453 A | 8/1989 | Ullman et al. |
| 4,877,586 A | 10/1989 | Devaney, Jr. et al. |
| 4,877,747 A | 10/1989 | Stewart |
| 4,895,017 A | 1/1990 | Pyke et al. |
| 4,916,056 A | 4/1990 | Brown, III et al. |
| 4,917,503 A | 4/1990 | Bhattacharjee |
| 4,940,734 A | 7/1990 | Ley et al. |
| 4,963,498 A | 10/1990 | Hillman et al. |
| 4,973,670 A | 11/1990 | McDonald et al. |
| 4,992,385 A | 2/1991 | Godfrey |
| 4,997,772 A | 3/1991 | Sutton et al. |
| 5,003,178 A | 3/1991 | Livesay |
| 5,023,053 A | 6/1991 | Finlan |
| 5,026,653 A | 6/1991 | Lee et al. |
| 5,035,863 A | 7/1991 | Finlan et al. |
| 5,055,265 A | 10/1991 | Finlan |
| 5,063,081 A | 11/1991 | Cozzette et al. |
| 5,064,619 A | 11/1991 | Finlan |
| 5,075,077 A | 12/1991 | Durley, III et al. |
| 5,076,094 A | 12/1991 | Frye et al. |
| 5,096,671 A | 3/1992 | Kane et al. |
| 5,100,238 A | 3/1992 | Nailor et al. |
| 5,114,676 A | 5/1992 | Leiner et al. |
| 5,120,662 A | 6/1992 | Chan et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,145,784 A | 9/1992 | Cox et al. |
| 5,152,758 A | 10/1992 | Kaetsu et al. |
| 5,156,953 A | 10/1992 | Litman et al. |
| 5,182,135 A | 1/1993 | Giesecke et al. |
| 5,196,350 A | 3/1993 | Backman et al. |
| 5,200,084 A | 4/1993 | Liberti et al. |
| 5,221,454 A | 6/1993 | Manian et al. |
| 5,225,935 A | 7/1993 | Watanabe et al. |
| 5,234,813 A | 8/1993 | McGeehan et al. |
| 5,235,238 A | 8/1993 | Nomura et al. |
| 5,238,815 A | 8/1993 | Higo et al. |
| 5,242,828 A | 9/1993 | Bergström et al. |
| 5,252,459 A | 10/1993 | Tarcha et al. |
| 5,262,299 A | 11/1993 | Evangelista et al. |
| 5,268,306 A | 12/1993 | Berger et al. |
| 5,314,923 A | 5/1994 | Cooke et al. |
| 5,316,727 A | 5/1994 | Suzuki et al. |
| 5,320,944 A | 6/1994 | Okada et al. |
| 5,321,492 A | 6/1994 | Detwiler et al. |
| 5,327,225 A | 7/1994 | Bender et al. |
| 5,330,898 A | 7/1994 | Bar-Or et al. |
| 5,342,759 A | 8/1994 | Litman et al. |
| 5,352,582 A | 10/1994 | Lichtenwalter et al. |
| 5,356,782 A | 10/1994 | Moorman et al. |
| 5,358,852 A | 10/1994 | Wu |
| 5,369,717 A | 11/1994 | Attridge |
| 5,374,563 A | 12/1994 | Maule |
| 5,376,255 A | 12/1994 | Gumbrecht et al. |
| 5,387,503 A | 2/1995 | Selmer et al. |
| 5,395,754 A | 3/1995 | Lambotte et al. |
| 5,415,842 A | 5/1995 | Maule |
| 5,418,136 A | 5/1995 | Miller et al. |
| 5,424,219 A | 6/1995 | Jirikowski |
| 5,432,057 A | 7/1995 | Litman et al. |
| 5,436,161 A | 7/1995 | Bergström et al. |
| 5,445,971 A | 8/1995 | Rohr |
| 5,451,683 A | 9/1995 | Barrett et al. |
| 5,455,475 A | 10/1995 | Josse et al. |
| 5,464,741 A | 11/1995 | Hendrix |
| 5,466,574 A | 11/1995 | Liberti et al. |
| 5,467,778 A | 11/1995 | Catt et al. |
| 5,468,606 A | 11/1995 | Bogart et al. |
| 5,482,830 A | 1/1996 | Bogart et al. |
| 5,482,867 A | 1/1996 | Barrett et al. |
| 5,484,867 A | 1/1996 | Lichtenhan et al. |
| 5,489,678 A | 2/1996 | Fodor et al. |
| 5,489,988 A | 2/1996 | Ackley et al. |
| 5,492,840 A | 2/1996 | Malmqvist et al. |
| 5,500,350 A | 3/1996 | Baker et al. |
| 5,504,013 A | 4/1996 | Senior |
| 5,508,171 A | 4/1996 | Walling et al. |
| 5,510,481 A | 4/1996 | Bednarski et al. |
| 5,512,131 A | 4/1996 | Kumar et al. |
| 5,512,432 A * | 4/1996 | Lapierre et al. ................. 435/5 |
| 5,514,559 A | 5/1996 | Markert-Hahn et al. |
| 5,514,785 A * | 5/1996 | Van Ness et al. ........... 536/22.1 |
| 5,516,635 A | 5/1996 | Ekins et al. |
| 5,518,689 A | 5/1996 | Dosmann et al. |
| 5,518,883 A | 5/1996 | Soini |
| 5,527,711 A | 6/1996 | Tom-Moy et al. |
| 5,534,132 A | 7/1996 | Vreeke et al. |
| 5,554,541 A | 9/1996 | Malmqvist et al. |
| 5,569,608 A | 10/1996 | Sommer |
| 5,571,684 A | 11/1996 | Lawrence et al. |
| 5,573,909 A | 11/1996 | Singer et al. |
| 5,585,279 A | 12/1996 | Davidson |
| 5,589,401 A | 12/1996 | Hansen et al. |
| 5,591,581 A | 1/1997 | Massey et al. |
| 5,596,414 A | 1/1997 | Tyler |
| 5,599,668 A | 2/1997 | Stimpson et al. |
| 5,618,732 A | 4/1997 | Pease et al. |
| 5,618,888 A | 4/1997 | Choi et al. |
| 5,620,850 A | 4/1997 | Bamdad et al. |
| 5,637,509 A | 6/1997 | Hemmilä et al. |
| 5,647,994 A | 7/1997 | Tuunanen et al. |
| 5,658,443 A | 8/1997 | Yamamoto et al. |
| 5,663,213 A | 9/1997 | Jones et al. |
| 5,670,381 A | 9/1997 | Jou et al. |
| 5,672,256 A | 9/1997 | Yee |
| 5,700,636 A | 12/1997 | Sheiness et al. |
| 5,726,064 A | 3/1998 | Robinson et al. |
| 5,731,147 A | 3/1998 | Bard et al. |

| Patent No. | Kind | Date | Inventor(s) | Class |
|---|---|---|---|---|
| 5,736,188 | A | 4/1998 | Alcock et al. | |
| 5,741,686 | A * | 4/1998 | Wagner et al. | 435/188 |
| 5,753,517 | A | 5/1998 | Brooks et al. | |
| 5,770,416 | A | 6/1998 | Lihme et al. | |
| 5,780,308 | A | 7/1998 | Ching et al. | |
| 5,795,470 | A | 8/1998 | Wang et al. | |
| 5,795,543 | A | 8/1998 | Poto et al. | |
| 5,811,526 | A | 9/1998 | Davidson | |
| 5,827,748 | A | 10/1998 | Golden | |
| 5,834,226 | A | 11/1998 | Maupin | |
| 5,837,429 | A | 11/1998 | Nohr et al. | |
| 5,837,546 | A | 11/1998 | Allent et al. | |
| 5,843,692 | A | 12/1998 | Phillips et al. | |
| 5,852,229 | A | 12/1998 | Josse et al. | |
| 5,876,944 | A | 3/1999 | Kuo | |
| 5,885,527 | A | 3/1999 | Buechler | |
| 5,906,921 | A | 5/1999 | Ikeda et al. | |
| 5,910,447 | A | 6/1999 | Lawrence et al. | |
| 5,910,940 | A | 6/1999 | Guerra | |
| 5,922,537 | A | 7/1999 | Ewart et al. | |
| 5,922,550 | A | 7/1999 | Everhart et al. | |
| 5,951,492 | A | 9/1999 | Douglas et al. | |
| 5,962,995 | A | 10/1999 | Avnery | |
| 5,993,805 | A * | 11/1999 | Sutton et al. | 424/94.1 |
| 6,004,530 | A | 12/1999 | Sagner et al. | |
| 6,020,047 | A | 2/2000 | Everhart | |
| 6,027,904 | A | 2/2000 | Devine et al. | |
| 6,027,944 | A | 2/2000 | Robinson et al. | |
| 6,030,792 | A | 2/2000 | Otterness et al. | |
| 6,030,840 | A | 2/2000 | Mullinax et al. | |
| 6,033,574 | A | 3/2000 | Siddiqi | |
| 6,048,623 | A | 4/2000 | Everhart et al. | |
| 6,060,256 | A | 5/2000 | Everhart et al. | |
| 6,080,391 | A | 6/2000 | Tsuchiya et al. | |
| 6,084,683 | A | 7/2000 | Bruno et al. | |
| 6,087,184 | A | 7/2000 | Magginetti et al. | |
| 6,099,484 | A | 8/2000 | Douglas et al. | |
| 6,103,537 | A | 8/2000 | Ullman et al. | |
| 6,117,090 | A | 9/2000 | Caillouette | |
| 6,136,549 | A | 10/2000 | Feistel | |
| 6,136,611 | A | 10/2000 | Saaski et al. | |
| 6,139,961 | A | 10/2000 | Blankenship et al. | |
| 6,151,110 | A | 11/2000 | Markart | |
| 6,165,798 | A | 12/2000 | Brooks | |
| 6,171,780 | B1 | 1/2001 | Pham et al. | |
| 6,171,870 | B1 | 1/2001 | Freitag | |
| 6,174,646 | B1 | 1/2001 | Hirai et al. | |
| 6,177,281 | B1 | 1/2001 | Manita | |
| 6,180,288 | B1 | 1/2001 | Everhart et al. | |
| 6,183,972 | B1 | 2/2001 | Kuo et al. | |
| 6,184,042 | B1 | 2/2001 | Neumann et al. | |
| 6,194,220 | B1 | 2/2001 | Malick et al. | |
| 6,200,820 | B1 | 3/2001 | Hansen et al. | |
| 6,221,238 | B1 | 4/2001 | Grundig et al. | |
| 6,221,579 | B1 | 4/2001 | Everhart et al. | |
| 6,234,974 | B1 | 5/2001 | Catt et al. | |
| 6,235,241 | B1 | 5/2001 | Catt et al. | |
| 6,235,471 | B1 | 5/2001 | Knapp et al. | |
| 6,235,491 | B1 | 5/2001 | Connolly | |
| 6,241,863 | B1 | 6/2001 | Monbouquette | |
| 6,242,268 | B1 | 6/2001 | Wieder et al. | |
| 6,255,066 | B1 | 7/2001 | Louderback | |
| 6,261,779 | B1 | 7/2001 | Barbera-Guillem et al. | |
| 6,268,222 | B1 | 7/2001 | Chandler et al. | |
| 6,270,637 | B1 | 8/2001 | Crismore et al. | |
| 6,271,040 | B1 | 8/2001 | Buechler | |
| 6,281,006 | B1 | 8/2001 | Heller et al. | |
| 6,284,472 | B1 | 9/2001 | Wei et al. | |
| 6,287,783 | B1 | 9/2001 | Maynard et al. | |
| 6,287,871 | B1 | 9/2001 | Herron et al. | |
| 6,294,392 | B1 | 9/2001 | Kuhr et al. | |
| 6,306,665 | B1 * | 10/2001 | Buck et al. | 436/530 |
| D450,854 | S | 11/2001 | Lipman et al. | |
| 6,331,438 | B1 | 12/2001 | Aylott et al. | |
| 6,348,186 | B1 | 2/2002 | Sutton et al. | |
| 6,362,011 | B1 | 3/2002 | Massey et al. | |
| 6,368,873 | B1 | 4/2002 | Chang et al. | |
| 6,368,875 | B1 | 4/2002 | Geisberg | |
| 6,387,707 | B1 | 5/2002 | Seul et al. | |
| 6,391,558 | B1 | 5/2002 | Henkens et al. | |
| 6,399,295 | B1 | 6/2002 | Kaylor et al. | |
| 6,399,397 | B1 | 6/2002 | Zarling et al. | |
| 6,407,492 | B1 | 6/2002 | Avnery et al. | |
| 6,411,439 | B2 | 6/2002 | Nishikawa | |
| 6,413,410 | B1 | 7/2002 | Hodges et al. | |
| 6,436,651 | B1 | 8/2002 | Everhart et al. | |
| 6,436,722 | B1 | 8/2002 | Clark et al. | |
| 6,444,423 | B1 | 9/2002 | Meade et al. | |
| 6,448,091 | B1 | 9/2002 | Massey et al. | |
| 6,451,607 | B1 | 9/2002 | Lawrence et al. | |
| 6,455,861 | B1 | 9/2002 | Hoyt | |
| 6,461,496 | B1 | 10/2002 | Feldman et al. | |
| 6,468,741 | B1 | 10/2002 | Massey et al. | |
| 6,472,226 | B1 | 10/2002 | Barradine et al. | |
| 6,479,146 | B1 | 11/2002 | Caruso et al. | |
| 6,509,085 | B1 | 1/2003 | Kennedy | |
| 6,509,196 | B1 | 1/2003 | Brooks et al. | |
| 6,511,814 | B1 | 1/2003 | Carpenter | |
| 6,556,299 | B1 | 4/2003 | Rushbrooke et al. | |
| 6,566,508 | B2 | 5/2003 | Bentsen et al. | |
| 6,573,040 | B2 | 6/2003 | Everhart et al. | |
| 6,579,673 | B2 | 6/2003 | McGrath et al. | |
| 6,582,930 | B1 | 6/2003 | Ponomarev et al. | |
| 6,585,939 | B1 | 7/2003 | Dapprich | |
| 6,613,583 | B1 | 9/2003 | Richter et al. | |
| 6,617,488 | B1 | 9/2003 | Springer et al. | |
| 6,663,833 | B1 | 12/2003 | Stave et al. | |
| 6,670,115 | B1 | 12/2003 | Zhang | |
| 6,720,007 | B2 * | 4/2004 | Walt et al. | 424/489 |
| 6,787,368 | B1 | 9/2004 | Wong et al. | |
| 6,815,218 | B1 | 11/2004 | Jacobson et al. | |
| 2001/0055776 | A1 | 12/2001 | Greenwalt | |
| 2002/0070128 | A1 | 6/2002 | Beckmann | |
| 2002/0101590 | A1 | 8/2002 | Shimaoka | |
| 2002/0146754 | A1 | 10/2002 | Kitawaki et al. | |
| 2002/0164659 | A1 | 11/2002 | Rao et al. | |
| 2003/0017615 | A1 | 1/2003 | Sidwell et al. | |
| 2003/0153011 | A1 * | 8/2003 | Bell | 435/7.9 |
| 2003/0178309 | A1 | 9/2003 | Huang et al. | |
| 2003/0232340 | A1 * | 12/2003 | Anderson | 435/6 |
| 2004/0014073 | A1 | 1/2004 | Trau et al. | |
| 2005/0170527 | A1 * | 8/2005 | Boehringer et al. | 436/514 |

FOREIGN PATENT DOCUMENTS

| | | |
|---|---|---|
| EP | 0205698 A1 | 12/1986 |
| EP | 0420053 A1 | 4/1991 |
| EP | 0437287 B1 | 7/1991 |
| EP | 0462376 B1 | 12/1991 |
| EP | 0469377 A2 | 2/1992 |
| EP | 0539035 A2 | 4/1993 |
| EP | 0539035 B1 | 4/1993 |
| EP | 0617285 A2 | 9/1994 |
| EP | 0617285 A3 | 9/1994 |
| EP | 0657737 A2 | 6/1995 |
| EP | 0657737 A3 | 6/1995 |
| EP | 0703454 A1 | 3/1996 |
| EP | 0711414 B1 | 5/1996 |
| EP | 0724156 A1 | 7/1996 |
| EP | 0745843 A2 | 12/1996 |
| EP | 0745843 A3 | 12/1996 |
| EP | 0833159 A2 | 4/1998 |
| EP | 0859230 A1 | 8/1998 |
| EP | 0898169 B1 | 2/1999 |
| EP | 1221616 A1 | 7/2002 |
| GB | 2273772 A | 6/1994 |

| WO | WO 8804777 A1 | 6/1988 |
| --- | --- | --- |
| WO | WO 9005305 A1 | 5/1990 |
| WO | WO 9105999 A2 | 5/1991 |
| WO | WO 9221769 A1 | 12/1992 |
| WO | WO 9221770 A1 | 12/1992 |
| WO | WO 9221975 A1 | 12/1992 |
| WO | WO 9301308 A1 | 1/1993 |
| WO | WO 9319370 A1 | 9/1993 |
| WO | WO 9406012 A1 | 3/1994 |
| WO | WO 9413835 A1 | 6/1994 |
| WO | WO 9415193 A1 | 7/1994 |
| WO | WO 9626435 A1 | 8/1996 |
| WO | WO 9709620 A1 | 3/1997 |
| WO | WO 9737222 A1 | 10/1997 |
| WO | WO 9810334 A1 | 3/1998 |
| WO | WO 9815831 A1 | 4/1998 |
| WO | WO 9827417 A1 | 6/1998 |
| WO | WO 9843086 A1 | 10/1998 |
| WO | WO 9910742 A1 | 3/1999 |
| WO | WO 9930131 A1 | 6/1999 |
| WO | WO 9936777 A1 | 7/1999 |
| WO | WO 9964864 A1 | 12/1999 |
| WO | WO 0019199 A1 | 4/2000 |
| WO | WO 0023805 A1 | 4/2000 |
| WO | WO 0034781 A1 | 6/2000 |
| WO | WO 0036416 A1 | 6/2000 |
| WO | WO 0046839 A2 | 8/2000 |
| WO | WO 0046839 A3 | 8/2000 |
| WO | WO 0047983 A1 | 8/2000 |
| WO | WO 0050891 A1 | 8/2000 |
| WO | WO 0078917 A1 | 12/2000 |
| WO | WO 0129559 A1 | 4/2001 |
| WO | WO 0138873 A2 | 5/2001 |
| WO | WO 0150129 A2 | 7/2001 |
| WO | WO 0150129 A3 | 7/2001 |
| WO | WO 0163299 A1 | 8/2001 |
| WO | WO 0171344 A2 | 9/2001 |
| WO | WO 0198765 A1 | 12/2001 |
| WO | WO 0198785 A2 | 12/2001 |
| WO | WO 02077646 A1 | 10/2002 |
| WO | WO 03005013 A1 | 1/2003 |
| WO | WO 03058246 A1 | 7/2003 |

OTHER PUBLICATIONS

Abstract of Japanese Patent No. JP 8062214, Mar. 8, 1996.
U.S. Appl. No. 10/035,013, filed Dec. 24, 2001, Kaylor, et al., Reading Device, Method, And System For Conducting Lateral Flow Assays.
U.S. Appl. No. 10/132,673, filed Apr. 25, 2002, Wei, et al., Internal Calibration System For Flow-Through Assays.
U.S. Appl. No. 10/132,421, filed Apr. 25, 2002, Song, et al., Polyelectrolytic Internal Calibration System Of A Flow-Through Assay.
U.S. Appl. No. 10/228,837, filed Aug. 27, 2002, Song, et al., Self-Calibration System For A Magnetic Binding Assay.
U.S. Appl. No. 10/228,838, filed Aug. 27, 2002, Song, et al., Fluidics-Based Assay Devices.
U.S. Appl. No. 10/228,836, filed Aug. 27, 2002, Song, et al., Membrane-Based Assay Devices.
U.S. Appl. No. 10/325,429, filed Dec. 19, 2002, Wei, et al., Self-Calibrated Flow-Through Assay Devices.
U.S. Appl. No. 10/308,926, filed Dec. 3, 2002, Yang, et al., Flow-Through Assay Devices.
U.S. Appl. No. 10/406,577, filed Apr. 3, 2003, Yang, et al., Assay Devices That Utilize Hollow Particles.
U.S. Appl. No. 10/286,342, filed Nov. 1, 2002, Song, et al., Membrane-Based Assay Devices That Utilize Time-Resolved Fluorescence.
U.S. Appl. No. 10/325,614, filed Dec. 19, 2002, Wei, et al., Reduction Of The Hook Effect In Membrane-Based Assay Devices.
PCT Search Report for PCT/US03/28628, Mar. 18, 2004.
PCT Search Report for PCT/US02/37653, Apr. 7, 2004.
PCT Search Report for PCT/US03/34543, Apr. 6, 2004.
PCT Search Report for PCT/US03/34544, Apr. 20, 2004.
Abstract of DE10024145A1, Nov. 22, 2001.
Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.
PCT Search Report and Written Opinion for PCT/US2004/013180, Aug. 17, 2004.
Article—*Whole Blood Capcellia CD4/CD8 Immunoassay for Enumeration of CD4+ and CD8+ Peripheral T Lymphocytes*, Dominique Carrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.
Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.
PCT Search Report and Written Opinion for PCT/US2004/006412, Sep. 28, 2004.
PCT Search Report and Written Opinion for PCT/US2004/006414, Sep. 28, 2004.
Article—*A conductometral biosensor for biosecurity*, Zarini Muhammad-Tahir and Evangelyn C. Alocilja, Biosensors & Bioelectronics, vol. 18, 2003, pp. 813-819.
Article—*A Disposable Amperometric Sensor Screen Printed on a Nitrocellulose Strip: A Glucose Biosensor Employing Lead Oxide as an Interference-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.
Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.
Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.
Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.
Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.
Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Article—*Inert Phosphorescent Nanospheres as Markers for Optical Assays*, Jens M. Kürner, Ingo Klimant, Christian Krause, Harald Preu, Werner Kunz, and Otto S. Wolfbeis, Bioconjugate Chem., vol. 12, No. 6, 2001, pp. 883-889.
Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.
Article—*Microfabrication by Microcontact Printing Of Self-Assembled Monolyaers*, James L. Wilbur, Armit Kumar, Enoch Kim, and George M. Whitesides, Advanced Materials, vol. 6, No. 7/8, 1994, pp. 600-604.
Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Kravchuk, Gely V. Ponomarev, Vitaly E. Lunev, and Alexander P. Savitsky, Journal of Immunological Methods 186, 1996, pp. 293-304.

Article—*Monofunctional Derivatives of Coproporphyrins for Phosphorescent Labeling of Proteins and Binding Assays*, Tómas C. O'Riordan, Aleksi E. Soini, and Dmitri B. Papkovsky, Analytical Biochemistry, vol. 290, 2001, pp. 366-375.

Article—*Near Infrared Phosphorescent Metalloporphrins*, Alexander P. Savitsky Anna V. Savitskaja, Eugeny A. Lukjanetz, Svetlana N. Dashkevich, and Elena A. 1997 Makarova, SPIE, vol. 2980, pp. 352-357, 1997.

Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.

Article—*Phosphorescent porphyrin probes in biosensors and sensitive bioassays*, D. B. Papkovsky, T. O'Riordan; and A. Soini, Biochemical Society Transactions, vol. 28, part 2, 2000, pp. 74-77.

Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.

Article—*Self-Assembled Monolayer Films for Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.

*AMI Screen Printers*—Product Information, 4 pages, obtained 2004.

U.S. Appl. No. 10/718,997, filed Nov. 21, 2003, Wei, et al. Extension Of The Dynamic Detection Range Of Assay Devices.

U.S. Appl. No. 10/719,976, filed Nov. 21, 2003, Xuedong Song, Method For Extending The Dynamic Detection Range Of Assay Devices.

U.S. Appl. No. 10/741,434, filed Dec. 19, 2003, Yang, et al., Laminated Assay Devices.

U.S. Appl. No. 10/742,589, filed Dec. 19, 2003, Yang, et al., Flow Control Of Electrochemical-Based Assay Devices.

U.S. Appl. No. 10/742,590, filed Dec. 19, 2003, Yang, et al., Flow-Through Assay Devices.

U.S. Appl. No. 10/718,989, filed Nov. 21, 2003, Xuedong Song, Membrane-Based Lateral Flow Assay Devices That Utilize Phosphorescent Detection.

U.S. Appl. No. 10/718,996, filed Nov. 21, 2003, Ning Wei, Method Of Reducing The Sensitivity Of Assay Devices.

U.S. Appl. No. 10/836,093, filed Apr. 30, 2004, David S. Cohen, Optical Detection Systems.

U.S. Appl. No. 10/790,617, filed Mar. 1, 2004, Boga, et al., Assay Devices Utilizing Chemichronic Dyes.

*Flow-Based Microimmunoassay*, Analytical Chemistry, vol. 73, No. 24, Mark A. Hayes, Nolan A. Polson, Allison, N. Phayre, and Antonia A. Garcia, pp. 5896-5902, Dec. 15, 2001.

Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.

Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.

Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.

Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.

Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.

Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.

Article—*Hollow latex particles: synthesis and applications*, Charles J. McDonald and Michael J. Devon, Advances in Colloid and Interface Science, Vo. 99, 2002, pp. 181-213.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.

Article—*Orientation dependence of surface segregation in a dilute Ni-Au alloy*, W . C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Volume Phase Transition of N-Alkylacrylamide Gels*, S. Saito, M. Konno, and H. Inomata, Advances in Polymer Science, vol. 109, 1992, pp. 207-232.

Article—*Molecular Design Temperature-Responsive Polymers as Intelligent Materials*, Teruo Okano, Advances in Polymer Science, pp. 179-197, 1993.

Article—*Molecular Gradients of ω-Substituted Alkanethiols on Gold: Preparation and Characterization*, Bo Liedberg and Pentti Tengvall, Langmuir, vol. 11, No. 10, 1995, pp. 3821-3827.

Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.

Article—*Analysis of electrical equivalent circuit of quartz crystal resonator loaded with viscous conductive liquids*, Journal of Electroanalytical Chemistry, vol. 379, 1994, pp. 21-33.

Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.

Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.

Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.

Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.

Article—*Intelligent Gels*, Yoshihito Osada and Simon B. Ross-Murphy, Scientific American, May 1993, pp. 82-87.

Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.

Article—*On the use of $Zx\text{-}LiNbO_3$ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*Probing of strong and weak electrolytes with acoustic wave fields*, R. Dahint, D. Grunze, F. Josse, and J. C. Andle, Sensors and Actuators B, vol. 9, 1992, pp. 155-162.

Article—*Patterned Condensation Figures as Optical Diffraction Gratings*, Amit Kumar and George M. Whitesides, Science, vol. 263, Jan. 7, 1994, pp. 60-62.

Article—*Stimuli-Responsive Poly(N-isopropylacrylamide) Photo- and Chemical-Induced Phase Transitions*, Advances in Polymer Science, pp. 50-65.

Article—*Quantitative Prediction of Surface Segregation*, M. P. Seah, Journal of Catalysts, vol. 57, 1979, pp. 450-457.

Article—*Sensing liquid properties with thickness-shear mode resonators*, S. J. Martin, G. C. Frye, and K. O. Wessendorf, Sensors and Actuators A, vol. 44, 1994, pp. 209-218.

Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.

Article—*New Approach to Producing Patterned Biomolecular Assemblies*, Suresh K. Bhatia, James J. Hickman, and Frances S. Ligler, J. Am. Chem. Soc., vol. 114, 1992, pp. 4433-4434.

Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article—*Patterned Functionalization of Gold and Single Crystal Silicon via Photochemical Reaction of Surface-Confined Derivatives of $(n^5-C_5H_5)Mn(CO)_3$*, Doris Kang and Mark S. Wrighton, Langmuir, vol. 7, No. 10, 1991, pp. 2169-2174.

Article—*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 2 pages, 1993.

Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages, 1995.

Article—*The Use of Self-Assembled Monolayers and a Selective Etch To Generate Patterned Gold Features*, Amit Kumar, Hans A. Biebuyck, Nicholas L. Abbott, and George M. Whitesides, Journal of the American Chemical Society, vol. 114, 1992, 2 pages.

Article—*Patterned Metal Electrodeposition Using an Alkanethiolate Mask*, T. P. Moffat and H. Yang, J. Electrochem. Soc., vol. 142, No. 11, Nov. 1995, pp. L220-L222.

Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.

Article—*Attempts of Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.

Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.

Article—*Application of rod-like polymers with ionophores as Langmuir-Blodgett membranes for Si-based ion sensors*, Sensors and Actuators B, 1992, pp. 211-216.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Responsive Gels: Volume Transitions I*, M. Ilavský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages, 1993.

*The colloidal state*, Introduction to Colloid and Surface Chemistry, $4^{th}$ Ed., 17 pages, 1992.

*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

*Working With FluoSpheres® Fluorescent Microspheres*, Properties and Modifications, Production Information from Molecular Probes, Mar. 9, 2001, pp. 1-5.

*FluoSpheres® Fluorescent Microspheres*, Production Information from Molecular Probes, Mar. 13, 2001, pp. 1-6.

*Factors influencing the formation of hollow ceramic microspheres by water extraction of colloidal droplets*, J. Mater. Res., vol. 10, No. 1, p. 84, 1996.

Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.

Article—*The Adsorptive Characteristics of Proteins for Polystyrene and Their Significance in Solid-Phase Immunoassays*, L.A. Cantaero, J. E. Butler, and J. W. Osborne, Analytical Biochemistry, vol. 105, 1980, pp. 375-382.

Article—*Latex Immunoassays*, Leigh B. Bangs, Journal of Clinical Immunoassay, vol. 13, No. 3, 1990, pp. 127-131.

\* cited by examiner

REDUCTION OF THE HOOK EFFECT IN ASSAY DEVICES

BACKGROUND OF THE INVENTION

Various analytical procedures and devices are commonly employed in flow-through assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

There are several well-known immunoassay methods that use immunoreactants labeled with a detectable component so that the analyte may be detected analytically. For example, "sandwich-type" assays typically involve mixing the test sample with detectable probes, such as dyed latex or a radioisotope, which are conjugated with a specific binding member for the analyte. The conjugated probes form complexes with the analyte. These complexes then reach a zone of immobilized antibodies where binding occurs between the antibodies and the analyte to form ternary "sandwich complexes." The sandwich complexes are localized at the zone for detection of the analyte. This technique may be used to obtain quantitative or semi-quantitative results. Some examples of such sandwich-type assays are described in by U.S. Pat. No. 4,168,146 to Grubb, et al. and U.S. Pat. No. 4,366,241 to Tom, et al.

However, many conventional "sandwich-type" assay formats encounter significant inaccuracies when exposed to relatively high analyte concentrations. Specifically, when the analyte is present at high concentrations, a substantial portion of the analyte in the test sample may not form complexes with the conjugated probes. Thus, upon reaching the detection zone, the uncomplexed analyte competes with the complexed analyte for binding sites. Because the uncomplexed analyte is not labeled with a probe, it cannot be detected. Consequently, if a significant number of the binding sites become occupied by the uncomplexed analyte, the assay may exhibit a "false negative." This problem is commonly referred to as the "hook effect."

Various techniques for reducing the "hook effect" in immunoassays have been proposed. For instance, U.S. Pat. No. 6,184,042 to Neumann, et al. describes one technique for reducing the hook effect in a sandwich assay. The technique involves incubating the sample in the presence of a solid phase with at least two receptors capable of binding to the analyte. The first receptor is an oligomer of a binding molecule selected from antibodies, antibody fragments and mixtures thereof. The second receptor is bound to or capable of being bound to a solid phase. The use of a soluble oligomeric antibody is said to reduce the "hook effect."

A need still exists, however, for an improved technique of reducing the "hook effect" in a simple, efficient, and relatively inexpensive manner.

SUMMARY OF THE INVENTION

In accordance with one embodiment of the present invention, a method for detecting the presence or quantity of an analyte residing in a test sample is disclosed. The method comprises:

i) providing a flow-through assay device comprising a porous membrane in communication with detection probes capable of generating a detection signal, the detection probes are conjugated with a specific binding member for the analyte, the porous membrane defines a detection zone within which a receptive material is immobilized;

ii) contacting a test sample containing the analyte with the conjugated detection probes so that analyte/probe complexes and uncomplexed analyte are formed;

iii) allowing the uncomplexed analyte to undergo non-specific binding; and iv) forming ternary complexes between the analyte/probe complexes and the receptive material within the detection zone, wherein the receptive material remains relatively free of the uncomplexed analyte.

In one embodiment, for instance, the uncomplexed analyte non-specifically binds to a domain present on at least a portion of the conjugated detection probes. In such instances, the conjugated detection probes containing the domain may individually define a hollow interior constituting from about 20% to about 100% of the spatial volume occupied by the probe. These "hollow" probes may have an interior surface and an exterior surface, wherein the interior surface includes the domain. In one embodiment, the domain is hydrophobic.

In accordance with another embodiment of the present invention, a flow-through assay device is disclosed for detecting the presence or quantity of an analyte residing in a test sample. The flow-through assay device comprises a porous membrane that is in communication with detection probes capable of generating a detection signal. The detection probes are conjugated with a specific binding member for the analyte and configured to combine with the analyte in the test sample when contacted therewith such that analyte/probe complexes and uncomplexed analyte are formed. The conjugated detection probes further contain a domain capable of non-specifically binding to the uncomplexed analyte. The porous membrane also defines a detection zone within which a receptive material is immobilized that is configured to bind to the analyte/probe complexes. The conjugated detection probes are capable of generating a detection signal while within the detection zone so that the amount of the analyte within the test sample is determined from said detection signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
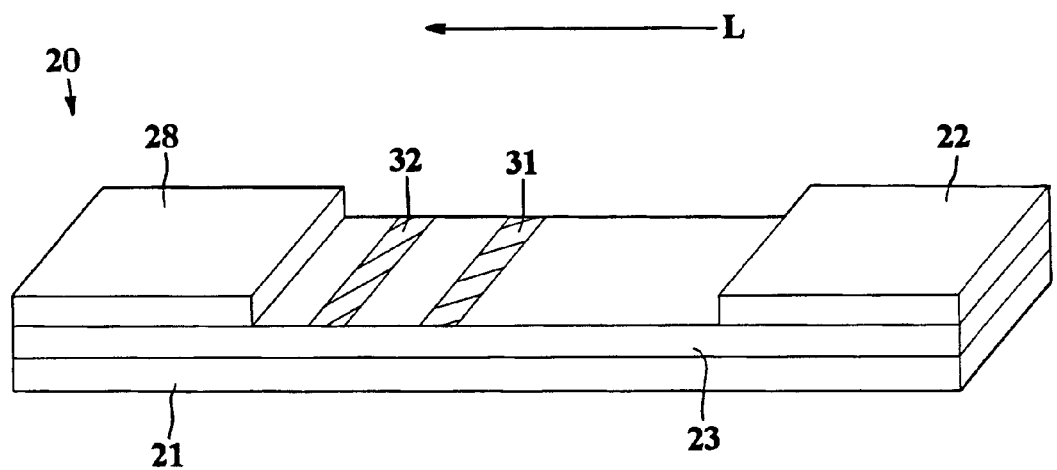
FIG. 1 is a perspective view of one embodiment of a flow-through assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes can include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; C-reactive protein; lipocalins; IgE antibodies; vitamin B2 micro-globulin; glycated hemoglobin (Gly. Hb); cortisol; digitoxin; N-acetyl-procainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a material suspected of containing the analyte. The test sample can be used directly as obtained from the source or following a pretreatment to modify the character of the sample. The test sample can be derived from any biological source, such as a physiological fluid, including, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The test sample can be pretreated prior to use, such as preparing plasma from blood, diluting viscous fluids, and the like. Methods of treatment can involve filtration, precipitation, dilution, distillation, mixing, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a membrane-based assay device for detecting the presence or quantity of an analyte residing in a test sample. The device utilizes conjugated probes that contain a specific binding member for the analyte of interest. The specific binding member preferentially complexes with the analyte within a test sample when contacted therewith. Excess analyte that remains uncomplexed with the specific binding member is allowed to undergo non-specific binding, such as to a domain (e.g., surface, molecule, etc.). As a result, the ability of the uncomplexed analyte to compete with the complexed analyte at the detection zone of the device is restricted. Thus, the incidence of "false negatives" is limited in a simple, efficient, and relatively inexpensive manner.

Referring to FIG. 1, for instance, one embodiment of a flow-through assay device 20 that may be formed according to the present invention will now be described in more detail. As shown, the device 20 contains a porous membrane 23 optionally supported by a rigid material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; nylon membranes; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 23 is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 may assist in promoting capillary action and fluid flow through the membrane 23.

To initiate the detection of an analyte within the test sample, a user may directly apply the test sample to a portion of the porous membrane 23 through which it may then travel.

Alternatively, the test sample may first be applied to a sampling pad (not shown) that is in fluid communication with the porous membrane 23. Some suitable materials that may be used to form the sampling pad include, but are not limited to, nitrocellulose, cellulose, porous polyethylene pads, and glass fiber filter paper. If desired, the sampling pad may also contain one or more assay pretreatment reagents, either diffusively or non-diffusively attached thereto.

In the illustrated embodiment, the test sample travels from the sampling pad (not shown) to a conjugate pad 22 that is placed in communication with one end of the sampling pad. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate accurate detection of the presence or absence of an analyte within the test sample, probes are applied at various locations of the device 20 for purposes of detection and/or calibration. As will be described in more detail below, a probe generally contains a particle or bead that is labeled with a signal-producing substance. For instance, various suitable labels include, but are not limited to, chromogens; catalysts; fluorescent compounds; chemiluminescent compounds; phosphorescent compounds; radioactive compounds; direct visual labels, including colloidal metallic (e.g., gold) and non-metallic particles, dye particles, enzymes or substrates, or organic polymer latex particles; liposomes or other vesicles containing signal producing substances; and so forth. For instance, some enzymes suitable for use as probes are disclosed in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable labels may be described in U.S. Pat. No. 5,670,381 to Jou, et al. and U.S. Pat. No. 5,252,459 to Tarcha, et al., which are incorporated herein in their entirety by reference thereto for all purposes.

In some embodiments, the label may contain a fluorescent compound that produces a detectable signal. The fluorescent compounds may be fluorescent molecules, polymers, dendrimers, particles, and so forth. Some examples of suitable fluorescent molecules, for instance, include, but are not limited to, fluorescein, europium chelates, phycobiliprotein, rhodamine and their derivatives and analogs. A visually detectable, colored compound may also be used as a label, thereby providing for a direct colored readout of the presence or concentration of the analyte in the sample without the need for further signal producing reagents.

Generally, the particles of the probes are modified with a specific binding member for the analyte of interest to form conjugated probes. Specific binding members refer to a member of a specific binding pair, i.e., two different molecules where one of the molecules chemically and/or physically binds to the second molecule. For instance, immunoreactive specific binding members may include antigens, haptens, aptamers, antibodies, and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

Figure 2:
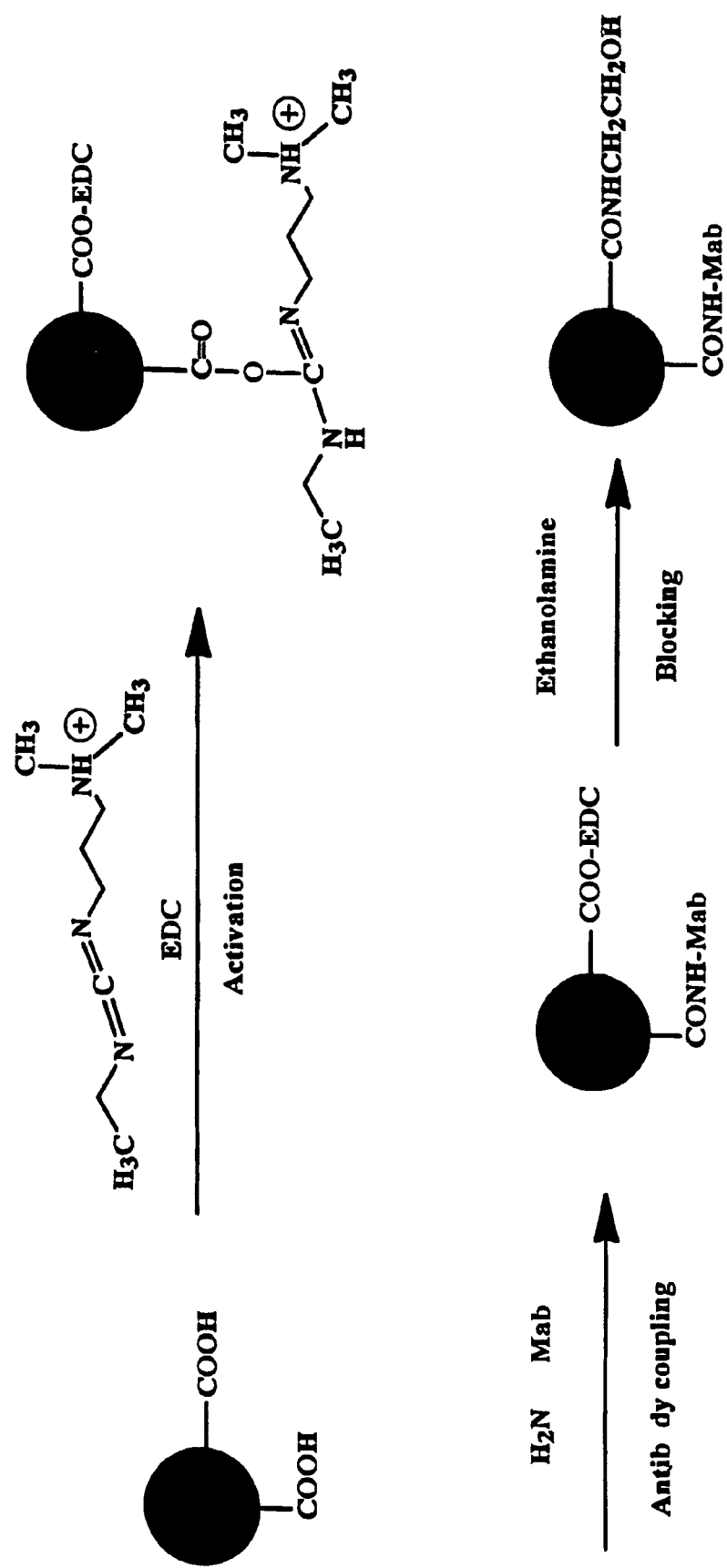
FIG. 2 is a graphical illustration of one embodiment for covalently conjugating an antibody to hollow probes.

The specific binding member may be attached to particles using any of a variety of well-known techniques. For instance, covalent attachment of the specific binding members to particles may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the particle may contain a relatively high surface concentration of polar groups. In addition, although particles are often functionalized after synthesis, in certain cases, such as poly(thiophenol), the particles are capable of direct covalent linking with a protein without the need for further modification. For example, referring to FIG. 2, one embodiment of the present invention for covalently conjugating a particle is illustrated. As shown, the first step of conjugation is activation of carboxylic groups on the particle surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). As shown, the resulting hollow particles can then be blocked with ethanolamine, for instance, to block any remaining activated sites. Overall, this process forms a conjugate, where the antibody is covalently attached to the particle. Besides covalent bonding, other attachment techniques, such as physical adsorption, may also be utilized in the present invention.

Referring again to FIG. 1, the assay device 20 may also contain a detection zone 31, on which is immobilized a receptive material that is capable of binding to the conjugated probes. For example, in some embodiments, the receptive material may be a biological receptive material. Such biological receptive materials are well known in the art and may include, but are not limited to, antigens, haptens, antibodies, protein A or G, avidin, streptavidin, secondary antibodies, and complexes thereof. In some cases, it is desired that these biological receptive materials are capable of binding to a specific binding member (e.g., antibody) present on the probes. In addition, it may also be desired to utilize various non-biological materials for the receptive material. For instance, in some embodiments, the receptive material may include a polyelectrolyte. The polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyidimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

The receptive material serves as a stationary binding site for the analyte/probe complexes. Specifically, analytes, such as antibodies, antigens, etc., typically have two binding sites. Upon reaching the detection zone 31, one of these binding sites is occupied by the specific binding member of the conjugated probe. However, the free binding site of the analyte may bind to the immobilized receptive material. Upon being bound to the immobilized receptive material, the complexed probes form a new ternary sandwich complex.

The detection zone 31 may generally provide any number of distinct detection regions so that a user may better determine the concentration of a particular analyte within a test sample. Each region may contain the same receptive materials, or may contain different receptive materials for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions may be disposed in the form of lines in a direction that is substantially parallel to the flow of the test sample through the assay device.

Although the detection zone 31 may indicate the presence of an analyte, it is often difficult to determine the relative concentration of the analyte within the test sample using solely a detection zone 31. Thus, the assay device 20 may also include a calibration zone 32. In this embodiment, the calibration zone 32 is formed on the porous membrane 23 and is positioned downstream from the detection zone 31. The calibration zone 32 is provided with a receptive material that is capable of binding to any remaining uncaptured probes that pass through the length of the membrane 23. The receptive material utilized in the calibration zone 32 may be the same or different than the receptive material used in the detection zone 31. Moreover, similar to the detection zone 31, the calibration zone 32 may also provide any number of distinct calibration regions in any direction so that a user may better determine the concentration of a particular analyte within a test sample. Each region may contain the same receptive materials, or may contain different receptive materials for capturing different probes.

The calibration regions may be pre-loaded on the porous membrane 23 with different amounts of the receptive material so that a different signal intensity is generated by each calibration region upon migration of the probes. The overall amount of binder within each calibration region may be varied by utilizing calibration regions of different sizes and/or by varying the concentration or volume of the receptive material in each calibration region. If desired, an excess of probes may be employed in the assay device 20 so that each calibration region reaches its full and predetermined potential for signal intensity. That is, the amount of probes that are deposited upon calibration regions are predetermined because the amount of the receptive material employed on the calibration regions is set at a predetermined and known level.

Regardless of the exact construction of the assay device, the conjugated probes contain a specific binding member for the analyte of interest. As a result, the conjugated probes are able to complex with the analyte when contacted therewith. Unfortunately, the amount of analyte present in the test sample may sometimes exceed the number of complexing sites provided by the specific binding members. Conventionally, this uncomplexed analyte would compete with the complexed analyte for the receptive material located at the detection zone 31. To counteract this "hook effect", the present invention utilizes preferential and non-specific binding. Specifically, the specific binding members of the probes preferentially bind to the analyte due to their high affinity for each other. When the specific binding members become fully occupied, the uncomplexed analyte in the test sample is then free to undergo additional binding.

Thus, in accordance with the present invention, the uncomplexed analyte undergoes "non-specific" binding. "Non-specific" binding generally refers to the intermolecular attraction of an analyte to a molecule or surface that is not a specific binding member for the analyte. Non-specific binding may be accomplished in a variety of ways. For example, in one embodiment, non-specific binding occurs through an attraction between two hydrophobic domains (e.g., surface, molecule, etc.). Namely, although the test sample in which the analyte is contained may be aqueous-based, the analyte itself contains hydrophobic domains. Thus, the hydrophobic domains of the uncomplexed analyte may non-specifically bind to another hydrophobic domain via a hydrophobic attraction. Hydrophobic interactions usually describe the attraction between non-polar groups/molecules/surface in an aqueous environment. It is believed that hydrophobic interaction occurs primarily through a free energy gain associated with the release of water molecules from a hydrophobic surface, i.e., water molecules contacting hydrophobic surfaces are in a less favorable state in terms of free energy compared with water molecules in the bulk phase. A more detailed discussion of hydrophobic interactions can be found Israelachvili and Wennerstrom, *Nature,* 1996, 379, 219-225; Israelachvili, *Intermolecular and Surface Forces* (2nd edition), Academic Press, 1991; and van Oss, *Interfacial Forces in Aqueous Media*, Marcel Dekker, 1994. Besides hydrophobic interaction, other non-specific binding may also occur. For example, electrostatic attractions, such as hydrogen bonding or ionic bonding, may occur to reduce the hook effect.

To avoid reducing the accuracy of the assay devices, it is generally desired that the non-specific binding technique employed be capable of distinguishing between complexed and uncomplexed analyte. In most embodiments, this distinction is accomplished by size differentiation. For example, the conjugated probes may contain pores that are sufficiently large to allow the smaller, uncomplexed analyte to pass therethrough, but small enough to block the larger, complexed analyte. For example, the pores may have an average size less than about 100 nanometers, in some embodiments from about 5 to about 100 nanometers, and in some embodiments, from about 0.1 to about 60 nanometers. By containing pores of a certain size, the conjugated probes can distinguish between complexed and uncomplexed analyte, allowing only the uncomplexed analyte to pass therethrough.

Further, in some embodiments, the conjugated probes may also be "hollow", i.e., individually define a hollow interior that constitutes from about 20% to about 100%, and in some embodiments, from about 30% to about 100% of the spatial volume occupied by the probe. Namely, a substantial portion of the spatial volume of each hollow probe remains empty. The presence of a hollow interior may provide a number of benefits. For instance, in some embodiments, the interior surface of the particles may be relatively hydrophobic. As a result, when the uncomplexed analyte migrates through the pores, it may non-specifically bind to the hydrophobic interior surface via a hydrophobic interaction. In one embodiment, the hollow probes are latex-based hollow beads formed from a polyacrylic acid shell polymer and a polystyrene core polymer. The polystyrene core polymer forms a hydrophobic interior surface that may non-specifically bind to the uncomplexed analyte. Although this attraction is not as strong as the bond formed between the analyte and specific binding member, it is believed that the attraction is nonetheless strong enough to inhibit the uncomplexed analyte from later competing with the complexed analyte at the detection zone. It should also be understood, however, that the interior surface may also be hydrophilic if desired.

In addition, uncomplexed analyte may sometimes get trapped within the interior surface of the hollow probes. In such instances, the uncomplexed analyte may be unable to compete with the complexed analyte for binding sites at the detection zone, regardless of whether substantial non-specific binding is present. For example, in one embodiment, the hollow probes may contain a hydrophilic interior surface and a hydrophobic exterior surface. Although some of the uncomplexed analyte will non-specifically bind to the exterior surface, it may also become trapped within the interior hydrophilic surface. Further, uncomplexed analyte that enters the hollow region of the probes may simply be slowed down, so it only reaches the detection zone 31 after the complexed analyte binds to the receptive material contained therein.

When utilized, the shape of the hollow probes may generally vary. In one particular embodiment, for instance, the hollow probes are spherical in shape. However, it should be understood that other shapes are also contemplated by the present invention, such as plates, rods, discs, bars, tubes, irregular shapes, etc. In addition, the size of the hollow probes may also vary. For instance, the average size (e.g., diameter) of the hollow particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have a average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

Although the shape and size of the particles may vary, as described above, it is often desired that the particles be "monodispersed" in that the particles within a given colloidal dispersion have approximately the same size and/or shape. Monodispersed hollow probes may provide improved reliability and reproducibility due to their generally uniform properties.

Besides their size and shape, the material(s) that form the hollow probes may also vary. The hollow probes may, for instance, be organic and/or inorganic in nature, and may be polymers, oligomers, molecules, and so forth. For example, the hollow particles may be formed from polymers such as polystyrene, (meth)acrylate polymers or copolymers, vinylidene chloride/acrylonitrile copolymers, etc. Other suitable hollow polymeric particles may be described in U.S. Pat. No. 4,427,836 to Kowalski, et al.; U.S. Pat. No. 4,480,042 to Craig, et al.; U.S. Pat. No. 4,973,670 to McDonald, et al.; U.S. Pat. No. 5,618,888 to Choi, et al.; and U.S. Pat. No. 6,139,961 to Blankenship, et al., which are incorporated herein in their entirety by reference thereto for all purposes. Still other hollow particles that may be used include inorganic materials, such as glass hollow particles. For instance, ECCOSPHERES® are hollow glass particles derived from sodium borosilicate commercially available from Emerson and Cuming Composite Materials, Inc. Other representative hollow particles derived from an inorganic material, include, for instance, silica hollow microspheres available under the trade name "SILICA BEADS S700" from Miyoshi Kasei, Inc. Other examples of hollow inorganic particles are described in U.S. Pat. No. 6,416,774 to Radin, et al., which is incorporated herein in its entirety by reference thereto for all purposes.

In one particular, embodiment, the hollow particles may be formed from one or more natural or synthetic latex polymers. Examples of such latex-based hollow particles are described in U.S. Pat. No. 5,663,213 to Jones, et al., which is incorporated herein in its entirety by reference thereto for all purposes, and commercially available from Rohm & Haas of Philadelphia, Pa. under the name SunSpheres®. The '213 patent describes the ability of such latex-based hollow particles, which are typically "micron-scale" in size, to be used for sun protection. However, the present inventors have also discovered that the latex-based hollow particles have unexpected utility in assay devices.

The latex-based hollow particles are typically formed from a core polymer and a shell polymer. The monomers used to form the core and shell polymers may generally vary. For instance, the shell polymer may be selected to provide a glass transition temperature ($T_g$) that is high enough to support the voids of the particle, e.g., such as greater than about 50° C., in some embodiments greater than about 60° C., and in some embodiments, greater than about 70° C. Some examples of suitable monomers that may be used to form the shell polymer include, but are not limited to, non-ionic ethylenically unsaturated monomers, monoethylenically unsaturated monomers containing at least one carboxylic acid group, and so forth.

The monomers that form the core polymer may include one or more monoethylenically unsaturated monomers containing at least one carboxylic acid group. In some embodiments, for instance, at least about 5 wt. % of the monoethylenically unsaturated monomers of the core polymer contain at least one carboxylic acid, based on total monomer weight of the core. Examples of suitable monoethylenically unsaturated monomers containing at least one carboxylic acid group include, but are not limited to, (meth)acrylic acid, acryloxypropionic acid, (meth)acryloxypropionic acid, itaconic acid, aconitic acid, maleic acid or anhydride, fumaric acid, crotonic acid, monomethyl maleate, monomethyl fumarate, monomethyl itaconate, and so forth. As used herein, the term "(meth)acrylic" is intended to serve as a generic expression embracing both acrylic and methacrylic.

In one embodiment, the monoethylenically unsaturated monomer containing at least one carboxylic acid group is copolymerized with one or more nonionic (e.g., having no ionizable group) ethylenically unsaturated monomers. Some suitable nonionic ethylenically unsaturated monomers include, but are not limited to, styrene, vinyltoluene, ethylene, vinyl acetate, vinyl chloride, vinylidene chloride, acrylonitrile, (meth)acrylamide, ($C_1$-$C_{20}$) alkyl or ($C_3$-$C_{20}$) alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, cleyl (meth)acrylate, palmityl (meth)acrylate, stearyl (meth)acrylate, and so forth.

The core polymer and/or shell polymer may optionally contain from about 0.1 wt. % to about 20 wt. %, and in some embodiments, from about 0.1 wt. % to about 3 wt. % of a polyethylenically unsaturated monomer based on the total monomer weight of the polymer. Examples of such unsaturated monomers include, but are not limited to, ethylene glycol di(meth)acrylate, allyl(meth)acrylate, 1,3-butanediol di(meth)acrylate, diethylene glycol di(meth)acrylate, trimethylolpropane tri(meth)acrylate, or divinylbenzene. If desired, the core polymer and/or shell polymer may contain from about 0.1 wt. % to about 60 wt. % butadiene based on the total monomer weight of the polymer.

To produce the void in the latex particles, the core is typically swelled with a swelling agent containing one or more volatile components. The swelling agent permeates the shell to swell the core. The volatile components of the swelling agent may then be removed by drying the latex particles, thereby causing a void to form within the latex particles. Although not required, the swelling agent may be an aqueous base. Examples of suitable aqueous bases include, but are not limited to, ammonia, ammonium hydroxide, alkali metal hydroxides, such as sodium hydroxide, or a volatile amine, such as trimethylamine or triethylamine. Removal of the templated core may also be accomplished in other ways, such as by calcining at elevated temperatures or by chemical reactions causing dissolution of the core material.

In addition to core-shell hollow particles, hollow particles may also be formed using other well-known techniques. For example, U.S. Pat. No. 6,479,146 to Caruso, et al., which is incorporated herein in its entirety by reference thereto for all purposes, describes hollow particles formed using electrostatic forces. In particular, hollow particles are formed using templated electrostatic layer-by-layer ("LBL") deposition of nanoparticle-polymer multilayers, followed by removal of the templated core. The template particles may, for instance, contain organic polymer latices, such as polystyrene or styrene copolymer latices.

The template particles are alternately coated with polyelectrolyte molecules and nanoparticles. The polyelectrolytes are usually polymers having ionically dissociable groups that may be a component or substituent of the polymer chain. The nanoparticles are typically ceramic particles, such as silicon dioxide, titanium dioxide, and zirconium dioxide optionally doped with other metal oxides; magnetic particles, such as $Fe_3O_4$; magneto-optical particles; nitridic ceramic particles, such as $Si_3N_4$, carbidic ceramic particles; metallic particles, such as gold, silver, and palladium; and sulfur or selene-containing particles, such as cadmium sulfide, cadmium selenide etc.

In one embodiment, the template particles are first coated with several layers of oppositely charged cationic and anionic polyelectrolytes before the alternating layers of nanoparticles and polyelectrolyte or the alternating nanoparticle layers are applied. Typically, the template particles are coated with at least two and up to six layers of oppositely charged cationic and anionic polyelectrolytes, e.g., with three layers. The outermost polyelectrolyte layer is typically oppositely charged with regard to the nanoparticle to be deposited. In most embodiments, the template particles are at least partially disintegrated after the coating has been completed. They can be dissolved in appropriate solvents and/or thermally dissolved (e.g., by calcination to temperatures of at least about 500° C.). After dissolution of the template particles, hollow shells remain that are composed of the nanoparticle material and optionally the polyelectrolyte material.

If desired, the electrostatically-formed particles may be modified to contain pores in at least one of the layers. Such pores can be formed by the polyelectrolytes or nanoparticles themselves. For instance, a high salt concentration of the medium used for the deposition of the polyelectrolyte may result in a high permeability of the shell wall. On the other hand, a high salt concentration of the medium used for the deposition of the nanoparticles (e.g., $SiO_2$) may result in a low permeability of the nanoparticles. Thus, by adjusting the salt concentrations in the deposition medium, the permeability of the shell can be controlled, as desired. Further, the permeability properties of the shell may be modified by selecting the conditions for decomposing the core, e.g., by selecting the temperature and heating conditions in a calcination procedure.

Figure 3:
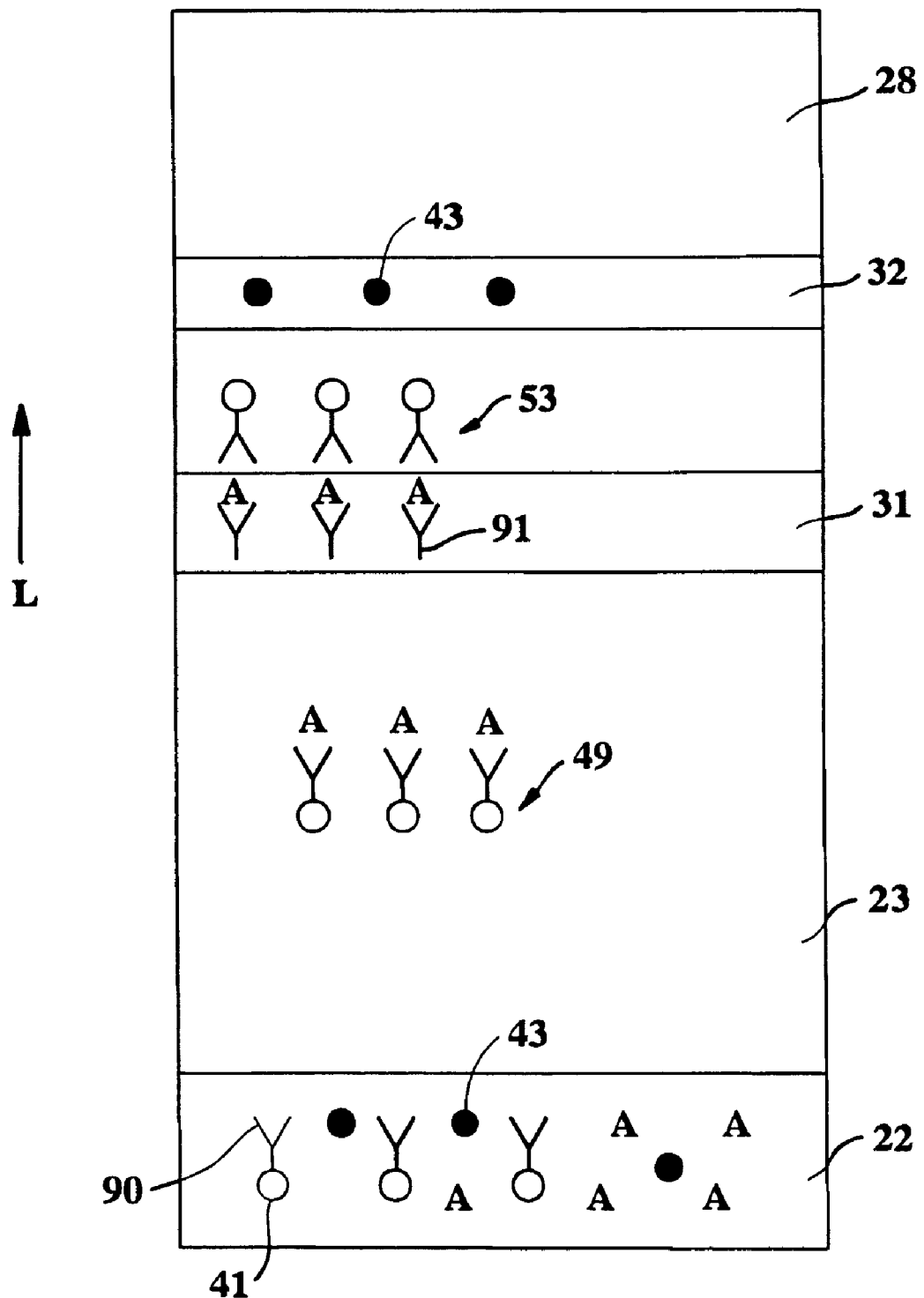
FIG. 3 is a schematic illustration of one embodiment of a flow-through assay device of the present invention.

In general, a variety of flow-through assay devices may be constructed according to the present invention. In this regard, various embodiments of the present invention will now be described in more detail. It should be understood, however, that the embodiments discussed below are only exemplary, and that other embodiments are also contemplated by the present invention. For instance, referring to FIG. 3, one particular embodiment in which detection probes 41 that contain hollow particles is shown. In this embodiment, the detection probes 41 are applied to the conjugate pad 22 and are thus capable of flowing through the device 20 (as indicated by the directional arrow L) when placed in communication with the test sample. The detection probes 41 are conjugated with a specific binding member 90 for an analyte A so that, upon contact with the analyte A, the probes 41 preferentially complex therewith to form analyte/probe complexes 49. Thereafter, any remaining analyte enters the interior of the probes 41 (not shown) where it may non-specifically bind to the interior surface of probes or otherwise become trapped therein.

The probe/analyte complexes 49 then flow from the conjugate pad 22 through the porous membrane 23 until they reach the detection zone 31 where they bind to a receptive material 91, such as an antibody, to form sandwich complexes 53. Because the uncomplexed analyte is trapped within the interior of the probes 41, it is unable to compete with the complexed analyte for the receptive material. Thus, at the detection zone 31, the amount of the analyte may be ascertained from the signal intensity of the detection probes 41. If desired, the device 20 may also employ calibration probes 43 that flow to the calibration zone 32 and bind to a receptive material (not shown), such as polyelectrolyte. In such instances, this signal intensity at the detection zone 31 may be calibrated by the signal intensity of the calibration probes 43 at the calibration zone 32. The signal intensities may be measured visually or through the aid of a device, such as a fluorescence reader.

Although various embodiments of device configurations have been described above, it should be understood, that a device of the present invention may generally have any configuration desired, and need not contain all of the components described above. Various other device configurations and/or assay formats, for instance, are described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

The present invention may be better understood with reference to the following examples.

Example 1

Figure 6:
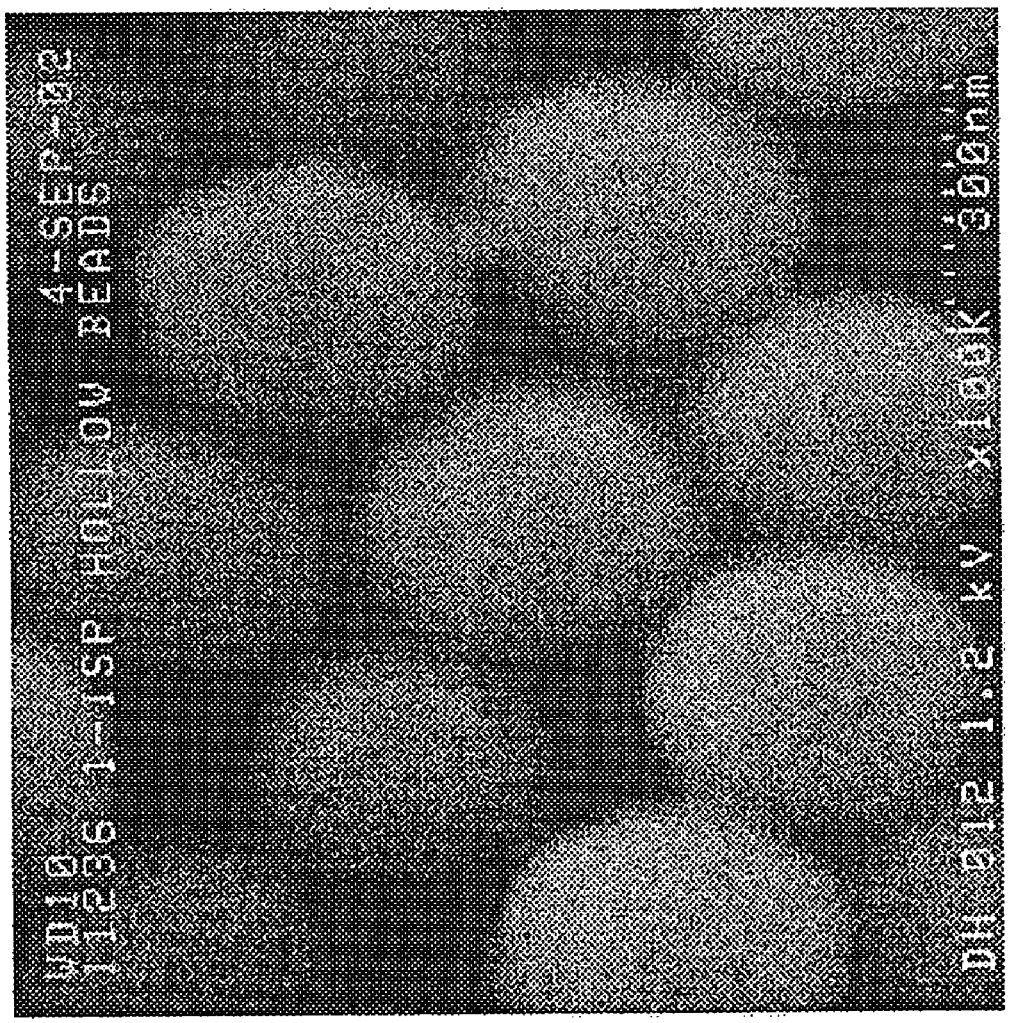
FIG. 6 is an SEM photograph (magnification of 100×) of the hollow particles utilized in Example 1.

SunSphere™ hollow particles (available from Rohm & Haas) were provided. The particles had an approximate solids content of 26% and an average measured size of 300 nanometers (based on SEM and particle sizer). An SEM photograph of such hollow particles is shown in FIG. 6. A 500-microliter solution of the particles was washed two times with 2-(N-morpholino)ethane sulfonic acid buffer (MES, pH of 5.3), 1 milliliter each. Into 1 milliliter of the particle/MES buffer solution, 30 milligrams of carbodiimmide (Polysciences, Inc.) were added. The reaction was allowed to occur for 10 minutes with rotation.

The hollow particles were then separated from the reaction solution and washed with 1 milliliter of a borated buffer. 1 milligram of a fluorescent dye, i.e., (5-(and-6)-((N-(5-aminopentyl)amino)carbonyl)tetramethylrhodamine-(tetramethylrhodamine cadaverine) was added to the borated buffer solution. The reaction was allowed to occur for 1 hour under constant rotation. After the reaction was complete, the supernatant was discarded and the hollow particles were washed with borate buffer until the supernatant solution became clear to remove any free fluorescent dye. The hollow particles were then re-suspended in 1 milliliter of borate buffer as the stock. From the stock solution, 100 microliters was taken out and diluted in 500 microliters borate buffer. Into this hollow particle solution, 100 microliters of monoclonal antibody Mab 5811 (BiosPacific, 6.4 milligrams per milliliter) were added and the reaction was allowed to occur for over 56 hours under constant rotation. The reaction was quenched with 200 microliters of ethanolamine, and the hollow particles were washed with PBS buffer and finally stored in 500 milliliters of storage buffer that contained 0.1 molar PBS, 0.15 molar NaCl, 1% BSA, 5% glycerol and 0.1% $NaN_3$.

Example 2

The ability to form a lateral flow assay in accordance with the present invention was demonstrated. Initially, a Millipore HF120 nitrocellulose membrane was laminated onto corresponding supporting cards having a length of approximately 30 centimeters. Aqueous CelQuat® 100-H (a cellulosic polyelectrolytic derivative available from National Starch & Chemical, Inc.) solution was stripped onto the membrane to form a control line. Monoclonal antibody Mab 5804 for C-reactive protein (1 milligram per milliliter, obtained from BiosPacific, Inc.) was immobilized on the porous membrane samples to form a detection line. The membrane samples were then dried for 1 hour at a temperature of 37° C. A cellulosic fiber wicking pad (Millipore Co.) was attached to one end of the membrane and cut into 4-millimeter half strips.

The half stick strips were put into various microwells where 20 microliters of the fluorescent hollow probe conjugates of Example 1 were mixed with 20 microliters of CRP antigen solutions or 20 microliters of TBS buffer. The microwell containing the buffer served as the negative control, while the microwell containing CRP antigen served as the positive sample. When the assay was finished, the half stick was taken out and the fluorescent intensity on the detection line was then measured using a Fluorolog III Spectrofluorometer (SPEX Industries, Inc., Edison, N.J.) with a right angle mode. The florescent intensity on the detection line was directly related to the quantity of the sandwich complex for the antigen, and therefore directly related to the concentration of the CRP antigen.

The results are shown below in Table 1, where "I" represents the signal intensity from the fluorescent hollow probes. The signal intensity for the negative control was considered background, and would be subtracted from the signal intensity for samples containing CRP analyte. It is noticed that, even at analyte concentrations of 5000 nanograms per milliliter, no hook effect was observed.

TABLE I

Signal Intensity Results

| Analyte (nanograms per milliliter) | Signal Intensity "I" |
|---|---|
| 0 (control) | 44 |
| 5 | 115 |
| 50 | 160 |
| 500 | 240 |
| 2500 | 320 |
| 5000 | 454 |

Example 3

For comparative purposes, an assay device was formed that did not utilize non-specific binding in accordance with the present invention. Initially, conjugated latex beads were formed by washing 125 microliters of blue latex particles (available from Bangs Laboratory, Inc., 10%, 0.3 microns in size) two times with 2-(N-morpholino)ethane sulfonic acid buffer (MES, pH of 5.3), 1 milliliter each. The latex particles were re-suspended into 500 microliters of MES buffer. 50 milligrams of carbodiimide were dissolved into 500 microliters of MES buffer and then mixed with the 500 microliters of the latex particle solution. The activation reaction was allowed to occur for 30 minutes. After the particles were separated from the reaction solution, they were washed twice with borate buffer. The particles were re-suspended into 1 milliliter of Borate buffer, and 45 microliters of monoclonal CRP antibody Mab 5811 was added and the reaction was taken place for 2½ hours. The latex particles were quenched with 1 milliliters of ethanolamine for 30 minutes and further washed with PBS buffer twice and finally stored in 1 milliliter of storage buffer.

To form the assay device, a Millipore HF120 nitrocellulose membrane was laminated onto corresponding supporting cards having a length of approximately 30 centimeters. Aqueous CelQuat® 100-H (a cellulosic polyelectrolytic derivative available from National Starch & Chemical, Inc.) solution was stripped onto the membrane to form a control line. Monoclonal antibody Mab 5804 for C-reactive protein (1 milligram per milliliter, BiosPacific, Inc.) was immobilized on the porous membrane samples to form a detection line. The membrane samples were then dried for 1 hour at a temperature of 37° C. A cellulosic fiber wicking pad (Millipore Co.) was attached to one end of the membrane and cut into 4-millimeter half strips. The half stick strips were put into various microwells where 19 microliters of 2% Tween 20 solution was mixed with 1 microliters of the conjugated latex beads, together with 20 microliters of CRP antigen solutions or 20 microliters of TBS buffer. The microwell containing the buffer served as the negative control, while the microwell containing CRP antigen served as the positive sample.

Figure 4:
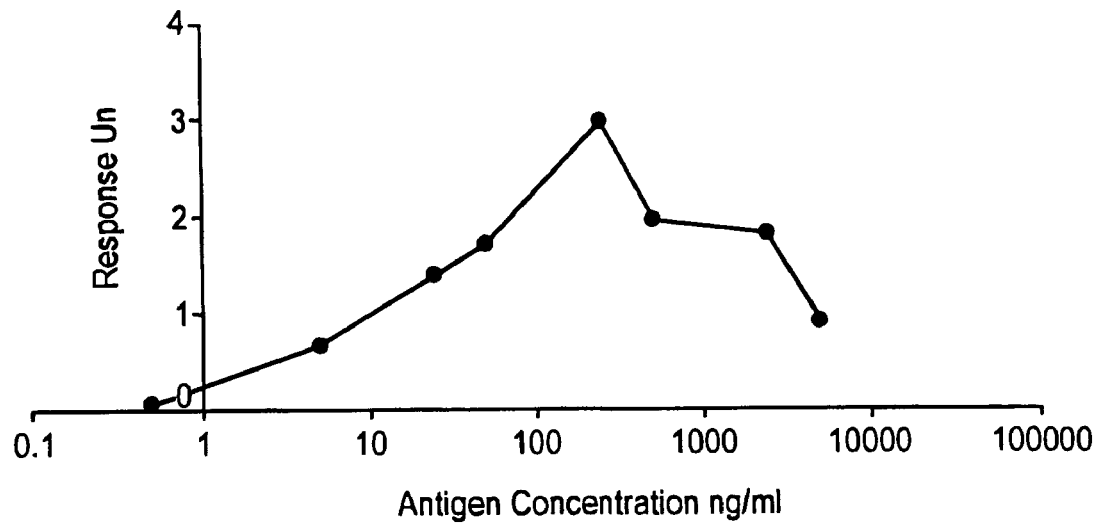
FIG. 4 is a graphical depiction of the results of Example 3.

When the assay was finished, the half stick was taken out and the intensity on the detection line was measured with a reflectance-based reader. The results are shown in FIG. 4, which shows intensity (pixels in area of detection line) versus analyte concentration. As indicated, the "hook effect" occurred at a low CRP concentration, i.e., about 250 to 500 nanograms per milliliter.

Example 4

For comparative purposes, an assay device was formed that did not utilize non-specific binding in accordance with the present invention. Initially, probes were formed by conjugating gold particles (at a wavelength of 530 nanometers, the absorbance=1) having a size of 40 nanometers with monoclonal antibody Mab 5811. To form the assay device, a Millipore HF120 nitrocellulose membrane was laminated onto corresponding supporting cards having a length of approximately 30 centimeters. Aqueous CelQuat® 100-H (a cellulosic polyelectrolytic derivative available from National Starch & Chemical, Inc.) solution was stripped onto the membrane to form a control line. Monoclonal antibody Mab 5804 for C-reactive protein (1 milligram per milliliter, BiosPacific, Inc.) was immobilized on the porous membrane samples to form a detection line. The membrane samples were then dried for 1 hour at a temperature of 37° C. A cellulosic fiber wicking pad (Millipore Co.) was attached to one end of the membrane and cut into 4-millimeter half strips. The half stick strips were put into various microwells where 19 microliters of 2% Tween 20 solution was mixed with 1 microliters of the conjugated gold particles, together with 20 microliters of CRP antigen solutions or 20 microliters of TBS buffer. The microwell containing the buffer served as the negative control, while the microwell containing CRP antigen served as the positive sample.

Figure 5:
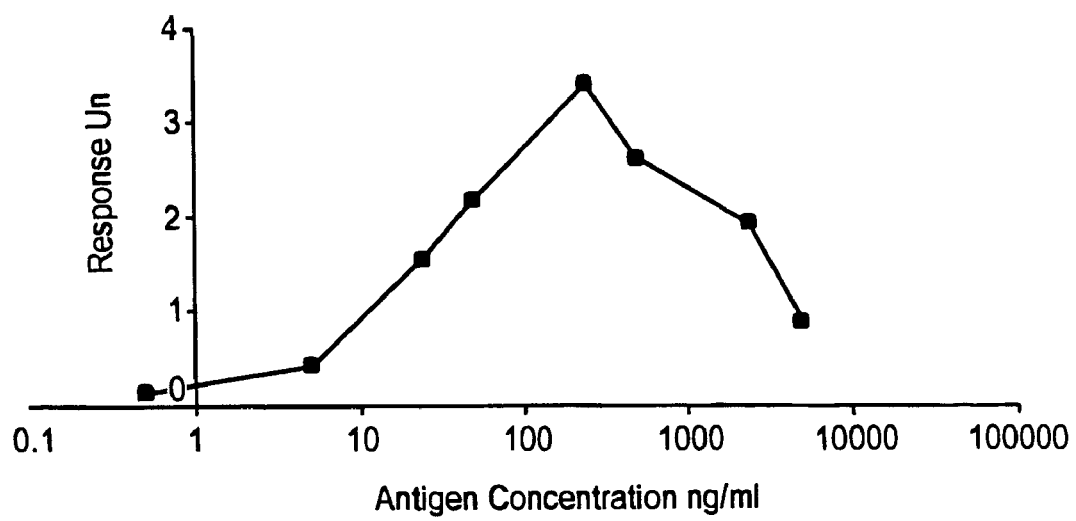
FIG. 5 is a graphical depiction of the results of Example 4.

When the assay was finished, the half stick was taken out and the intensity on the detection line was measured with a reflectance-based reader. The results are shown in FIG. 5, which shows intensity (pixels in area of detection line) versus analyte concentration. As indicated, the "hook effect" occurred at a low CRP concentration, i.e., about 250 to 500 nanograms per milliliter.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A flow-through assay device for detecting the presence or quantity of an analyte residing in a test sample, the flow-through assay device comprising:

a porous membrane in communication with particles that are labeled with a signal-producing substance and conjugated with a specific binding member, the specific binding member being capable of preferentially binding to the analyte to form analyte/probe complexes, wherein the particles comprise pores that have an average size of less than about 100 nanometers and block the analyte/probe complexes but allow an uncomplexed analyte to pass therethrough, and further wherein the particles contain a hollow interior within which a domain is located, the domain non-specifically binding to the uncomplexed analyte that passes through the pores, the hollow interior constituting at least about 20% of the spatial volume occupied by the particle, wherein the particles comprise a shell polymer containing a nonionic ethylenically unsaturated monomer and an ethylenically unsaturated monomer that includes at least one carboxylic acid group;

wherein the porous membrane of the flow-through assay device defines a detection zone within which a receptive material is immobilized, the receptive material being configured to bind to the analyte/probe complexes, and further wherein the particles are capable of generating a detection signal when present within the detection zone that corresponds to the presence of the analyte within the test sample.

2. The flow-through assay device of claim 1, wherein the hollow interior constitutes at least about 30% of the spatial volume occupied by the particle.

3. The flow-through assay device of claim 1, wherein the domain is located on a surface of the particles.

4. The flow-through assay device of claim 1, wherein the particles have a spherical shape.

5. The flow-through assay device of claim 1, wherein the particles are formed by electrostatic layer deposition.

6. The flow-through assay device of claim 1, wherein the particles comprise the shell polymer and a core polymer, the core polymer containing polystyrene.

7. The flow-through assay device of claim 1, wherein the average size of the particles ranges from about 0.1 nanometers to about 100 microns.

8. The flow-through assay device of claim 1, wherein the average size of the particles ranges from about 1 nanometer to about 10 microns.

9. The flow-through assay device of claim 1, wherein the pores have an average size of from about 5 to about 100 nanometers.

10. The flow-through assay device of claim 1, wherein the pores have an average size of from about 0.1 to about 60 nanometers.

11. The flow-through assay device of claim 1, wherein the signal-producing substance is selected from the group consisting of chromogens, catalysts, fluorescent compounds, chemiluminescent compounds, phosphorescent compounds, radioactive compounds, direct visual labels, liposomes, and combinations thereof.

12. The flow-through assay device of claim 1, wherein the specific binding member is selected from the group consisting of antibodies, antigens, haptens, biotin, avidin, streptavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof.

13. The flow-through assay device of claim 1, wherein the receptive material is selected from the group consisting of antigens, haptens, antibodies, protein A or G, avidin, streptavidin, secondary antibodies, and complexes thereof.

14. The flow-through assay device of claim 6, wherein the domain is hydrophobic.

15. The flow-through assay device of claim 1, wherein the ethylenically unsaturated monomer that includes at least one carboxylic acid includes (meth)acrylic acid, acryloxypropionic acid, (meth)acryloxypropionic acid, itaconic acid, aconitic acid, maleic acid or anhydride, fumaric acid, crotonic acid, monomethyl maleate, monomethyl fumarate, monomethyl itaconate, or a combination thereof.

* * * * *